United States Patent [19]
Miki et al.

[11] Patent Number: 5,078,682
[45] Date of Patent: Jan. 7, 1992

[54] LIQUID TRANSFUSION APPARATUS

[75] Inventors: Fumio Miki, Nara, Japan; Edmund D. D'Silva, Highland Park, Ill.; Grace M. Esche, Algonquin, Ill.; Michael S. Fairchild, Lake Zurich, Ill.; Larry Kramer, Chicago, Ill.; Kenneth M. Lynn, McHenry, Ill.

[73] Assignee: Sharp Kabushiki Kaisha, Osaka, Japan

[21] Appl. No.: 442,999

[22] Filed: Nov. 28, 1989

[30] Foreign Application Priority Data

Nov. 30, 1988 [JP] Japan .................... 63-157108[U]

[51] Int. Cl.⁵ ............................................ A61M 5/00
[52] U.S. Cl. ......................................... 604/65; 604/67; 128/DIG. 13
[58] Field of Search ..................... 604/65, 67, 131, 151, 604/153; 128/DIG. 12, DIG. 13; 73/717, 723, 866.3; 364/413.01, 413.02; 417/63

[56] References Cited

U.S. PATENT DOCUMENTS

| | | | |
|---|---|---|---|
| 4,080,653 | 3/1978 | Barnes, Jr. et al. | 364/413.02 |
| 4,227,420 | 10/1980 | Lamadrid | 73/756 |
| 4,394,862 | 7/1983 | Shim | 604/67 |
| 4,526,574 | 7/1985 | Pekkarinen | 604/52 |
| 4,547,771 | 10/1985 | Rockwood et al. | |
| 4,648,869 | 3/1987 | Bobo, Jr. | 604/49 |
| 4,670,006 | 6/1987 | Sinnet et al. | 604/26 |
| 4,846,792 | 7/1989 | Bobo, Jr. | 604/50 |
| 4,959,050 | 9/1990 | Bobo, Jr. | 604/49 |
| 4,979,940 | 12/1990 | Bobo, Jr. | 604/50 |

FOREIGN PATENT DOCUMENTS

| | | |
|---|---|---|
| 0096849 | 12/1983 | European Pat. Off. . |
| 0156788 | 10/1985 | European Pat. Off. . |
| 0341364 | 11/1989 | European Pat. Off. . |
| 3519908 | 12/1986 | Fed. Rep. of Germany . |
| 62-236558 | 10/1987 | Japan . |

Primary Examiner—Stephen C. Pellegrino
Assistant Examiner—Steven J. Shumaker
Attorney, Agent, or Firm—David G. Conlin; Donald Brown

[57] ABSTRACT

The liquid transfusion apparatus according to the present invention includes a setting device adapted to respectively set a normal level of pressure of the fed liquid and an upper alarm level of pressure of the fed liquid, calculating unit for calculating a percentage of a difference between the detected level of pressure of the liquid and the set normal level to a difference between the set upper alarm level and the set normal level, and display unit for displaying the calculated percentage. The liquid transfusion apparatus is very useful for monitoring the pressure of the liquid which is being administered to a patient.

11 Claims, 2 Drawing Sheets

LIQUID TRANSFUSION APPARATUS

BACKGROUND OF THE INVENTION

1. Field of the Invention

The present invention relates to a liquid transfusion apparatus adapted to forcibly transfusing a transfusion liquid by a pressure generated by a pump or the like.

2. Description of the Related Art

In general, a liquid transfusion apparatus which forcibly feeds a transfusion liquid by a pressure offers advantages over gravity type of liquid transfusion apparatus, such as greater degree of freedom of control of the flow rate of the liquid to be transfused, higher stability of the flow rate, and so forth. When this type of liquid transfusion apparatus is used for transfusion treatment, there is a risk that the pressure at which the transfusion liquid is supplied to the patient's body is dangerously changed due to, for example, inadequate prick of the needle, accidental removal of the needle from the blood vessel as a result of movement of the patient, bending of the transfusion tube, and so forth.

In order to avert from such a danger, the known liquid transfusion apparatus feeding forcibly the transfusion liquid is provided with means for monitoring the pressure of the transfusion liquid during the transfusion treatment. More specifically, the pressure of the transfusion liquid is detected by a pressure sensor disposed at an intermediate portion of the transfusion tube, and the pressure signal from the pressure sensor is converted into a digital signal by an A/D converter, and thus the converted signal is delivered to a display unit which digitally displays the pressure level corresponding to the digital signal. The pressure signal from the pressure sensor also is supplied to a comparator which compares the pressure level with a predetermined reference level When the reference level is exceeded by the pressure level, an alarm is sounded to inform that the pressure of the transfusion liquid is abnormally high.

In this known apparatus, the display unit displays the level of the pressure of the transfusion liquid in, for example, psi (pound square inch) as it is. Thus, there is no means which would show how much the pressure of the transfusion liquid is deviated from a normal pressure level, and how much a margin of pressure is left until the alarm is sounded. Thus, a doctor or a nurse has to determine the margin of pressure which is left until the alarm is sounded, by reading the level displayed on the display unit and comparing the read level with the normal pressure level or a pressure level at which the alarm is to be sounded. Namely, it has been impossible to determine, at a glance of the display unit, the deviation from the normal pressure level and the degree of margin of pressure which is left until the alarm is to be sounded, at a glance of the display unit. In addition, the allowable limit level of the pressure of the transfusion liquid varies according to the nature of the patient. Namely, the maximum allowable pressure for adults is different from that for infants. This means that the pressure level at which the alarm is to be sounded must be changed according to the type of the patient. Once the pressure level at which the alarm is to be sounded is changed, the doctor or the nurse is obliged to reconsider the degree of margin pressure which is left until the alarm is sounded. Thus, the known liquid transfusion apparatus cannot be used conveniently and, hence, an improvement has been required.

SUMMARY OF THE INVENTION

Accordingly, an object of the present invention is to provide a liquid transfusion apparatus which enables a doctor or a nurse to recognize, at a glance, the amount of deviation of the pressure of the transfusion liquid from the normal pressure level or the degree of margin of pressure which is left until the alarm is to be sounded.

According to the present invention, the object of the present, invention is attained by a liquid transfusion apparatus comprising: a transfusion tube for a transfusion liquid to be pricked into human body; a liquid feed unit disposed at the feed tube for feeding to the human body the liquid in the feed tube; a pressure detection unit disposed in the feed tube, in a downstream side of the liquid feed means for detecting a pressure level of the fed liquid; a setting unit adapted to respectively set a normal level of the pressure level of the fed liquid and an upper alarm level of the pressure level of the fed liquid; a calculating unit adapted to calculate a percentage of a difference between the detected level of the pressure level of the liquid and the set normal level to a difference between the set upper alarm level and the set normal level; and a display unit electrically connected to the calculating means for displaying the calculated percentage.

The liquid transfusion apparatus according to the present invention is provided with a setting unit adapted to respectively set a normal level of the pressure level of the fed liquid and an upper alarm level of the pressure level of the fed liquid, a calculating unit adapted to calculate a percentage of a difference between the detected level of the pressure level of the liquid and the set normal level to a difference between the set upper alarm level and the set normal level, and a display unit electrically connected to the calculating means for displaying the calculated percentage.

According to the invention, therefore, a doctor or a nurse can recognize, at a glance, the amount of deviation of the present pressure of the transfusion liquid from the normal pressure level and the degree of margin of pressure which is left until the alarm is to be sounded, when he or she looks at the percentage displayed on the liquid transfusion apparatus.

Therefore, any abnormal pressure rise is easily detected before the alarm is sounded, thereby enabling the nurse or the doctor to take any recovery measure such as re-pricking with the needle or straightening of the bent transfusion tube. In addition, the normal pressure level and the pressure level at which the alarm is to be sounded can easily be changed through an operation of the setting means as required according to the type of the patient and to the existing state of use of the liquid transfusion apparatus.

Thus, the invention provides a liquid transfusion apparatus which is easy to use and which can overcome the above-described problems of the prior art.

Further objects and advantages of the present invention will be apparent from the following description of the preferred embodiment of the invention as illustrated in the accompanying drawings.

DESCRIPTION OF THE PREFERRED EMBODIMENT

Figure 1:
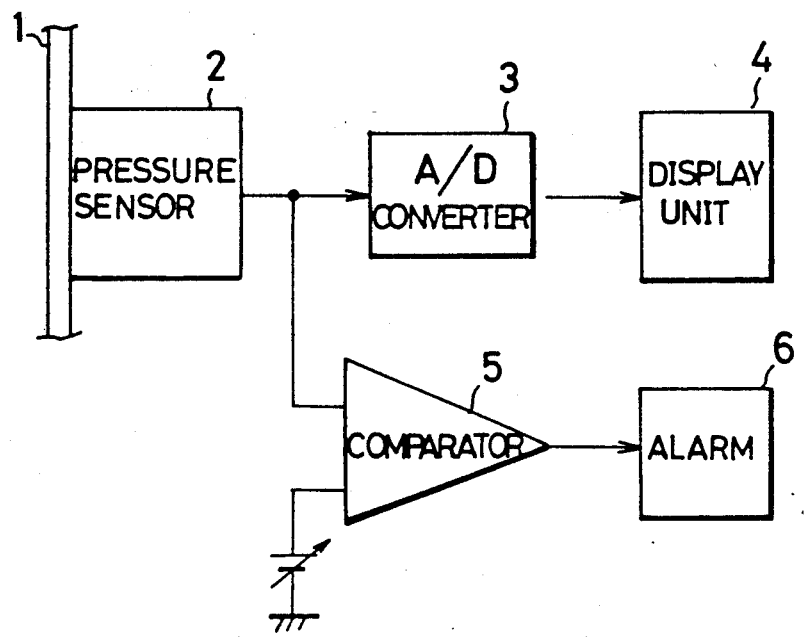
FIG. 1 is a block diagram of an embodiment of a conventional liquid transfusion apparatus.

FIG. 1 is a block diagram of the conventional liquid transfusion apparatus adapted to forcibly transfusing a transfusion liquid by pressure. This conventional apparatus has a monitoring means which enables the pressure of the transfusion liquid to be monitored. More specifically, the pressure of the transfusion liquid in a transfusion tube 1 is detected by a pressure sensor 2 provided at an intermediate portion of the tube 1, and the pressure signal from the pressure sensor 2 is converted into a digital signal by an A/D converter 3. The digitized signal is displayed as a pressure level in a display unit 4. The pressure signal from the pressure sensor 2 also is supplied to a comparator 5 which compares a pressure level corresponding to the pressure signal with a predetermined reference level. When the reference level is exceeded by the pressure level, an alarm 6 is sounded to inform that the pressure of the transfusion liquid is abnormally high.

Figure 2:
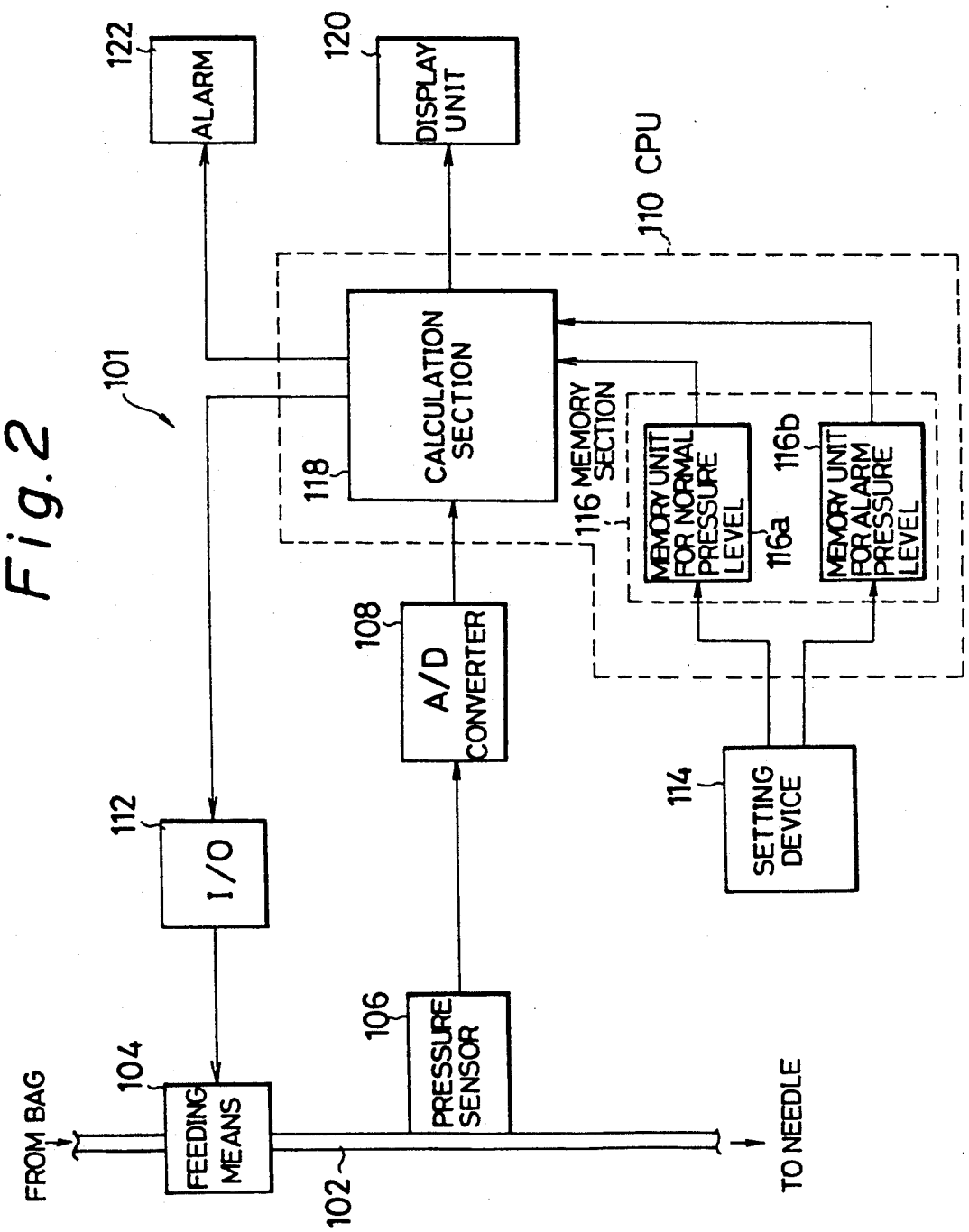
FIG. 2 is a block diagram of an embodiment of the liquid transfusion apparatus.

FIG. 2 is a block diagram of the liquid transfusion apparatus according to the present invention. The apparatus 101 has a transfusion tube 102 which is connected at its upstream end to a bag (not shown) for receiving a transfusion liquid and at its downstream end to a needle (not shown). Feeding means 104 for feeding the transfusion liquid is provided at an intermediate portion of the tube 102. Also provided at an intermediate portion of the tube 102 is a pressure sensor 106 for sensing the pressure of the transfusion liquid which is being transfused through the tube 102 by the pressure generated by the feeding means 104. The feeding means 104 may be a transfusion pump including eccentric cams provided on the shaft of the pump and fingers provided on the outer circumference of the eccentric cams so as to press the tube 102. The word "transfusion liquid" used in the present specification includes a blood and a medical liquid. In the illustrated embodiment, an electromagnetic induction sensor is used as the pressure sensor 106. This, however, is not exclusive and a strain-gauge-type sensor, capacitance-type sensor and a diaphragm-type sensor capable of directly or indirectly sensing the pressure can be used as the pressure sensor 106.

The pressure sensor 106 senses the pressure of the transfusion liquid transfused through the tube 102 and delivers a pressure signal to an A/D converter 108. The A/D converter 108 converts the pressure signal from the sensor 106 into digital signal and delivers it as an output signal to a CPU (Central Processing Unit) 110 which is adapted to process the digital signal received from the A/D converter 108. An interface section 112, which is electrically connected to the CPU 110, receives a control signal from the CPU 110 and delivers the same to the feeding means 104. A setting device 114 electrically connected to the CPU 110 is adapted to be able to set a normal pressure level for the transfusion liquid and a pressure level at which an alarm is to be sounded.

The CPU 110 has a memory section 116 for storing respectively the normal pressure level and an alarm pressure level at which an alarm is to be sounded, which pressure levels are set by the setting device 114, and a calculation section 118 for calculating the percentage of the difference between the pressure of the transfusion liquid and the normal pressure level to the difference between the normal pressure level and the alarm pressure level on the basis of the normal pressure level and the alarm pressure level, which are stored in the memory section 116, when receiving the pressure signal from the pressure sensor 106 through A/D converter 108. The memory section 116 includes a memory unit 116a for storing the normal pressure level and a memory unit 116b for storing the alarm pressure level. The display unit 120, which is electrically connected to the calculation section 118, is adapted to display a calculation result on the basis of a calculation result signal from the calculation section 118. The alarm 120 is connected to the calculation section 118 and operates in accordance with the calculation result signal from calculation section 118 so as to sound an alarm when the pressure of the liquid detected by the pressure sensor 106 has exceeded the alarm pressure level.

The operation of the described embodiment is as follows.

Before the use of the apparatus 1, the normal pressure level (Pn) for the pressure of the liquid to be transfused and the alarm pressure level (Pa) at which the alarm is to be sounded are set by means of the setting device 114. For instance, the alarm pressure level (Pa) is set at 17 psi for adults and at 7 psi for infants. The normal pressure level (Pn) and the alarm pressure level (Pa) set by the setting device 114, are respectively stored in the memory unit 116a for the normal pressure level and in the memory unit 116b for the alarm pressure level.

An outer diameter of the tube 102 varies according to a change in the internal pressure of the tube 102, with the result that the level of the pressure signal from the pressure sensor 106 also changes. The pressure signal outputted from the pressure sensor 106 is digitized through the converter 108 and the thus digitized pressure signal is supplied from the converter 108 to the calculation section 118 of the CPU 110. The calculation section 118 then calculate a percentage (P%) given by the following formula on the basis of the normal pressure level (Pn) and the alarm pressure level (Pa), which levels are stored in the memory section 116, and the digitized pressure signal which is representative of the pressure level (Px) of transfusion liquid and is supplied from the converter 108.

$$P\% = \{(Px - Pn)/(Pa - Pn)\} \times 100$$

Figure 3A:
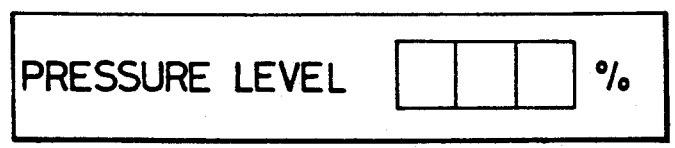
FIGS. 3a and 3b are illustrative view of a display unit used in the embodiment shown in FIG. 2.
Figure 3B:
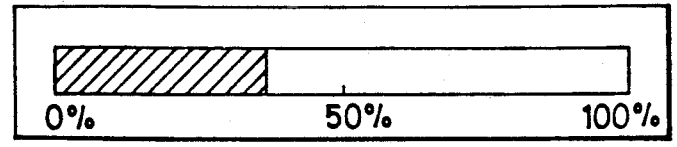

The result of the calculation is delivered from the calculation section 118 to the display unit 120 so that the display unit 120 displays the level of the percentage (%) in the form of a numerical representation as shown in FIG. 3a or in the form of a bar graph as shown in FIG. 3b.

The doctor or the nurse can therefore recognize, at a glance of the percentage displayed in the display unit 120, the amount of deviation of the pressure of the transfusion liquid from the normal pressure level or the degree of margin of pressure which is left until the alarm is to be sounded.

When the alarm pressure level at which an alarm is to be sounded is exceeded by the pressure level corresponding to the pressure signal from the pressure sensor 106, the calculation section 118 delivers an alarm signal to the alarm 120 so that the alarm is sounded to inform that the pressure of the transfusion liquid has been raised to an abnormal level. At the same time, the feeding means 104 is stopped by a control signal from the CPU 110 through the interface section 112 to thereby stop the supply of the liquid.

Many widely different embodiments of the present invention may be constructed without departing from the spirit and scope of the present invention. It should be understood that the present invention is not limited to the specific embodiment described in the specification, except as defined in the appended claims.

What is claimed is:

1. A liquid transfusion apparatus comprising:
a transfusion tube for transfusing liquid into a human body;
a liquid feed means attached to said transfusion tube for feeding said liquid into said transfusion tube;
a pressure detecting means attached to said transfusion tube down stream of said transfusion tube with respect to said liquid feed means for detecting a pressure level of said liquid in said transfusion tube;
a setting means capable of setting a normal pressure level
and an upper alarm pressure level of said liquid in said transfusion tube;
a calculating means electrically coupled to said pressure detecting means and coupled to said setting means for calculating a percentage of a difference between said detected pressure level detected by said pressure detecting means and said normal pressure level set by said setting means with respect to a difference between said upper pressure level and said normal pressure level set by said setting means; and
display means electrically coupled to said calculating means for displaying said percentage calculated by said calculating means.

2. A liquid transfusion apparatus according to claim 1, wherein said pressure detecting means includes a pressure sensor for detecting said pressure level of said liquid in said transfusion tube and for outputting an analog signal representative of said detected pressure level of said liquid, and A/D converter electrically coupled to said pressure sensor for converting said analog signal output from said pressure sensor into a digital signal.

3. A liquid transfusion apparatus according to claim 2, wherein said pressure sensor is an electromagnetic induction sensor.

4. A liquid transfusion apparatus according to claim 2, wherein said pressure sensor is a capacitive type sensor.

5. A liquid transfusion apparatus according to claim 1, wherein said setting means comprises a first memory unit for storing said normal pressure level set by said setting means, and a second memory unit for storing said upper alarm pressure level set by said setting means.

6. A liquid transfusion apparatus according to claim 2, wherein said pressure sensor is a diaphragm type sensor.

7. A liquid transfusion apparatus according to claim 1, wherein said calculating means further comprises an interface electrically coupled to said calculating means and to said liquid feed means, said interface capable of outputting a control signal generated from said calculating means to said liquid feed means so that said liquid feed means is controlled by said control signal.

8. A liquid transfusion apparatus according to claim 1, wherein said calculating means further comprises an alarm unit for sounding an alarm at a time when said detected pressure level of said liquid exceeds said upper alarm pressure level set by said setting means.

9. A liquid transfusion apparatus according to claim 1, wherein said liquid feed means comprises a transfusion pump having eccentric cams attached to a rotational shaft thereof, and fingers fixed to an outer circumferential surface of said eccentric cams so as to press said transfusion tube.

10. A liquid transfusion apparatus according to claim 1, wherein said display means is capable of displaying said percentage calculated by said calculating means in numerals.

11. A liquid transfusion apparatus according to claim 1, wherein said display means is capable of displaying said percentage calculated by said calculating means by a bar graph.

* * * * *